United States Patent [19]

Khan et al.

[11] Patent Number: 5,753,254
[45] Date of Patent: May 19, 1998

[54] THERAPEUTIC AGENTS CONTAINING THYROID HORMONES

[75] Inventors: Karrar Ahmad Khan; Alan Smith, both of Nottingham, Great Britain

[73] Assignee: Knoll Aktiengesellschaft, Ludwigshafen, Germany

[21] Appl. No.: 682,783

[22] PCT Filed: Jan. 30, 1995

[86] PCT No.: PCT/EP95/00321

§ 371 Date: Jul. 31, 1996

§ 102(e) Date: Jul. 31, 1996

[87] PCT Pub. No.: WO95/20953

PCT Pub. Date: Aug. 10, 1995

[30] Foreign Application Priority Data

Feb. 1, 1994 [GB] United Kingdom ............ 9401892

[51] Int. Cl.⁶ .................................... A61K 9/14
[52] U.S. Cl. ............... 424/439; 424/442; 424/484; 424/485; 424/488; 574/561
[58] Field of Search ................ 424/400, 407, 424/439, 442, 484, 485, 488; 514/561; 574/5, 554, 561

[56] References Cited

U.S. PATENT DOCUMENTS

| | | | |
|---|---|---|---|
| 3,090,724 | 5/1963 | Bowen | 167/55 |
| 5,464,632 | 11/1995 | Cousin et al. | 424/465 |

FOREIGN PATENT DOCUMENTS

| | | |
|---|---|---|
| 680863 | 2/1964 | Canada . |
| 371 466 | 6/1990 | European Pat. Off. . |
| 435 684 | 7/1991 | European Pat. Off. . |
| 550 108 | 7/1993 | European Pat. Off. . |
| 923171 | 4/1963 | United Kingdom . |
| 1296510 | 12/1972 | United Kingdom . |
| 88/04551 | 6/1988 | WIPO . |

*Primary Examiner*—Neil S. Levy
*Attorney, Agent, or Firm*—Keil & Weinkauf

[57] ABSTRACT

There is disclosed a solid fast dispersing dosage form of a pharmaceutical composition suitable for oral administration comprising: a therapeutic agent which comprises one or more compound thyroid hormone or hormones; from about 80% to about 99.9% of disintegrating agent by mass; from about 0.01% to about 10% of flavoring agent by mass; and from about 0.1% to about 5% mass of lubricating agent by mass; which has utility in the treatment of disorders associated with the improvement of the thyroid hormone function in animals including human beings.

12 Claims, No Drawings

THERAPEUTIC AGENTS CONTAINING THYROID HORMONES

This invention relates to novel pharmaceutical compositions comprising one or more thyroid hormones, and to their use in the treatment of disorders associated with impairment of the thyroid hormone functions in animals including human beings.

Pharmaceutical compositions comprising solid fast dispersing dosage forms for oral administration have recently become available. The dosage forms are prepared by freeze drying, a relatively slow process, which involves the use of expensive and complicated equipment. Furthermore, fast dispersing dosage forms produced by freeze drying are very friable and extremely moisture sensitive, which makes them difficult to package. For example, when presented in a conventional blister pack they are not sufficiently hard to retain their integrity when a force is applied to break the package seal and eject them from the blister. Such tablets are also unsuitable for conventional packing into bottles. Known freeze dried fast dispersing dosage forms have the further disadvantage that they are difficult to prepare other than as large tablets.

Therefore it is an object of the invention to provide a solid fast dispersing oral dosage form for a pharmaceutical composition as described herein which avoids all or some of the disadvantages of known freeze dried rapidly dispersing dosage forms whilst retaining all or some of the advantages of fast dispersing dosage forms over more conventional solid oral dosage forms.

These advantages include good patient compliance as fast dispersing dosage forms are easy to ingest as they disintegrate readily and quickly in the mouth within seconds imparting a pleasant sensation to the mouth. This can be particularly useful for patients such as children or the elderly who have difficulty in swallowing, as no extra liquid (eg water) is required to take these oral dosage forms. Fast dispersing oral dosage forms have the further advantage that the thyroid hormone active ingredient is presented to the gastro-intestinal tract in a finely divided particulate form which favours optimal and consistent absorption into the body.

To improve convenience and patient compliance the oral dosage forms of the present invention may be made of a mass typically ten times smaller than possible for freeze-dried dosage forms. Small oral dosage forms have the further advantage of minimising the amount of diluents ingested particularly when the therapeutic agent is present in very small amounts, for example the microgram quantities per unit dose required if the therapeutic agent is thyroid hormone.

Thyroid hormones as described are useful in the treatment of disorders associated with improvement of the thyroid hormone function in animals including human beings for example myxedema, cretinism or obesity. Thyroid hormones can be prepared synthetically as the biologically active 1-enantiomer or can be isolated direct from the thyroid gland of animals.

Therefore the present invention provides a solid fast dispersing dosage form of a pharmaceutical composition suitable for oral administration comprising: a therapeutic agent which comprises at least one thyroid hormone; from about 80% to about 99.9% of disintegrating agent; from about 0.01% to about 10% of flavouring agent; and from about 0.1% to about 5% of lubricating agent, all percentages being percentage mass of ingredient by total mass of the composition (known hereinafter as 'by mass').

Surprisingly, the present invention provides pharmaceutical compositions giving the above stated advantages of fast dispersing oral dosage forms without freeze drying. Freeze drying is a time consuming and expensive process requiring significant capital investment in specialised plant and machinery and high maintenance and operating costs. The production of the solid fast dispersing oral dosage form of the present invention by using simple formulation and processing technology results in major cost savings over production of known rapidly dispersing oral dosage forms. The lubricating agent is added to the composition to aid compression of the solid dosage form In order to improve palatability and patient compliance it has also been found that the composition must comprise a flavouring agent. Solid fast dispersing oral dosage forms of the invention are less friable than freeze-dried formulations and may be made into smaller dosage forms than is possible with freeze-dried formulations. Compositions of the present invention have a suitably long shelf life, and disperse in the mouth rapidly in a fine particulate form with no gritty texture. They are easy and pleasant to administer.

Thyroid hormones comprise the following:
L-3,5,3',5'-tetraiodothyronine (levothyroxine or LT4);
L-3,5,3'-triiodothyronine (liothyronine or LT3);
L-3,3',5'-triiodothyronine (LrT3);
L-3,5-diiodothyronine (LT2); or mixtures thereof. As used herein the term thyroid hormone should be understood to include all pharmaceutically acceptable salts thereof, preferably sodium salts.

Thyroid hormones may exist as one or more polymorphic forms (for example one or more crystalline forms, amorphous forms, phases, solid solutions and/or mixtures thereof) and the therapeutic agent may include each pharmaceutically acceptable polymorphic form of thyroid hormones and/or mixtures thereof.

Thyroid hormones may also exist in the form of solvates (for example hydrates) and the therapeutic agent may include each solvate of thyroid hormones and/or mixtures thereof.

Preferably the therapeutic agent is present in the composition in an amount per unit dose from about 0.1 µg to about 10,000 µg, more preferably from about 1 µg to about 1000 µg, most preferably, if the therapeutic agent is $LT_4$, from about 25 µg to about 300 µg.

It may be beneficial for any of the ingredients of compositions of the present invention (including the therapeutic agent) to be in the form of particles of very small size, for example as obtained by fluid energy milling. Alternatively the therapeutic agent may be bound (for example by sorption, incorporation and/or chemically) to nanoparticles which are collodial polymeric particles of a size typically less than 1 micron. The distribution of such nanoparticles in the body and hence the sites of delivery of the therapeutic agent can be effected by coating the surface of the nanoparticles appropriately (for example with surfactants or antibodies). The therapeutic agent in the solid dosage form of the present invention may, if desired, be associated with other compatible, pharmacologically active ingredients.

Preferably the disintegrating agent comprises a blend of at least two components and each component may independently comprise one or more of the following ingredients: pharmaceutical grade starch (eg maize starch), modified starch (eg pre-gelled starch and/or sodium starch glycollate), agar, bentonite, cellulose, microcrystalline cellulose, methylcellulose, carmellose, croscarmellose sodium, alginic acid, guar gum, silicon dioxide and sodium lauryl sulphate; more preferably one or more of pharmaceutical grade starch and microcrystalline cellulose. Preferably the disintegrating agent is present in an amount from about 80% to about 99%, more preferably from about 85% to about 98% by mass of the composition.

Preferably the flavouring agent comprises one or more of the following:

- a sweetening agent which may be a nutritive or non-nutritive sweetener preferably sodium saccharin or aspartame;
- a peppermint oil and/or fruit flavour;
- a flavour enhancing agent; or
- an ingredient or ingredients which may induce the formation of saliva, preferably a pharmaceutically acceptable acid, more preferably an organic acid, most preferably an acid selected from citric and malic acid.

Preferably the flavouring agent is present in an amount from about 0.1% to about 5%, more preferably from about 1% to about 3%, by mass of the composition.

Preferably the lubricating agent is selected from one or more of the following ingredients: magnesium stearate, calcium stearate, stearic acid and mixtures thereof; more preferably magnesium stearate. Preferably the lubricating agent is present in an amount from about 0.1% to about 1% by mass of the composition.

The disintegrating agent may be the sole diluent in the composition, or the composition may also comprise one or more additional inert diluent or diluents, which may be selected from one or more of the following ingredients: lactose, powdered sugar, sucrose, pharmaceutical grade starch, kaolin, talc, and pharmaceutically acceptable calcium salts; more preferably selected from sucrose and pharmaceutical grade starch, talc, calcium phosphate and calcium sulphate. The total amount of diluent (including the disintegrating agent) may be present in an amount from about 90% to about 99.9%, preferably from about 95% to about 99%, more preferably from about 95% to about 98%, by mass of the composition.

The solid oral dosage forms of the invention may further comprise one or more of the following optional ingredients which are pharmaceutically acceptable:

- binders, for example starch, gelatin, sugars (such as sucrose, molasses or lactose), and/or natural and synthetic gums (such as acacia, sodium alginate, extract of Irish moss, carboxymethylcellulose, methylcellulose, ethylcellulose, polyethylene glycol, waxes, microcrystalline cellulose or polyvinylpyrrolidione);
- colouring agents, for example conventional pharmaceutically acceptable dyes;
- orally acceptable preservatives;
- anti-oxidants; and
- one or more pharmaceutically acceptable effervescent couple or couples (such as an acid and a carbonate, preferably sodium carbonate and/or sodium bicarbonate) to aid disintegration and improve mouth feel.

The optional ingredients may be present in an amount from a trace amount to about 10% by mass of the composition.

Preferably solid oral dosage forms of the present invention may have a hardness in the range from about 1 to about 6 kp, more preferably from about 1 to about 5 kp. It will be appreciated by a person skilled in the art that these ranges should not be considered as limiting, because the actual hardness of a specific solid dosage form of the present invention will vary according to the particular formulation and equipment used to prepare the dosage form. The practical limits for the hardness of solid dosage forms of the invention are governed by the minimum hardness required to survive production, packaging, transport and removal from the packaging and the maximum hardness which still provides an acceptable mouth feel.

A further aspect of the present invention provides use of a thyroid hormone in the preparation of the pharmaceutical compositions described herein for the treating of disorders associated with an impairment of the thyroid hormone function in animals including human beings.

A still further aspect of the present invention provides a method of treating disorders associated with an impairment of the thyroid hormone function in animals including human beings, which comprises administering to a patient in need thereof a therapeutically and/or prophylactically effective amount of a composition according to the present invention.

Whilst the precise amount of the therapeutic agent administered in the treatment described above will depend on a number of factors, for example the severity of the condition, the age and past medical history of the patient, and always lies within the sound discretion of the administering medical practitioner or veterinary a suitable daily dose of a thyroid hormone or administration to animals, including human beings, may generally be from about 0.1 µg to about 10,000 µg, preferably from about 1 µg to about 1000 µg, more preferably if the thyroid hormone is $LT_4$ from about 25 µg to about 300 µg given in a single dose or in divided doses at one or more times during the day. Compositions of the present invention may be prepared in unit dosage form, therefore each solid oral dosage form may comprise from about 0.1 µg to about 10,000 µg, preferably from about 1 µg to about 1000 µg, more preferably, if the therapeutic agent is $LT_4$, from about 25 µg to about 300 µg (for example 25 µg, 50 µg, 75 µg or 100 µg) of a thyroid hormone.

Pharmaceutical compositions of the present invention may be used in adjunctive therapy with one or more other compounds having activity in the treatment of disorders associated with an impairment of the thyroid hormone function in animals including human beings. It will be appreciated that the term treatment as used herein includes prophylactic use of the pharmaceutical composition of the present invention for example to protect against conditions such as hypothyroidism, in animals including human beings.

The compositions of the present invention may be prepared by blending of the components or by wet or dry granulation. The blend or granulation is then compressed into tablets.

A yet further aspect of the present invention provides a method for the manufacture of the solid oral dosage forms of the invention comprising the steps of:

(a) forming a first mixture by blending in intimate admixture one or more disintegrant or disintegrants with a therapeutic agent comprising one or more thyroid hormone or hormones;

(b) forming a second mixture by blending in intimate admixture one or more disintegrant or disintegrants with a flavouring agent and a lubricating agent;

(c) combining the first and second mixtures to form a pharmaceutical composition; and (d) compressing the composition from step (c) to form a fast dispersing solid oral dosage form.

The invention will now be illustrated by the following non-limiting examples in which % m/m indicates the amount of ingredient is given as percentage by mass of the ingredient per total mass of the composition. The percentages may not total 100% due to rounding.

EXAMPLE 1

| Fast dispersing formulation | |
|---|---|
| Ingredient | % m/m |
| Maize starch powder (disintegrant) A | 33.15 |
| Microcrystalline cellulose (Avicel PH101) (disintegrant) | 15.00 |
| L-thyroxine | therapeutically effective [µg] amounts |
| Maize starch powder (disintegrant) | 34.15 |
| Microcrystalline cellulose (Avicel PH101) (disintegrant) B | 15.00 |
| Citric acid powder (saliva inducing agent) | 2.00 |
| Aspartame (sweetener) | 0.2 |
| Magnesium stearate powder (lubricant) | 0.5 |

The ingredients marked A were mixed together and granulated. The powders marked B were mixed together and the resultant powder was mixed with the granules from A to coat them. Optionally permitted colours may be added at this stage. The coated granules were then compressed into tablets each containing 50 µg levothyroxine sodium on an anhydrous basis, each tablet having a hardness in the range from 1 to 3 kp. The resulting tablets were hard enough to survive in conventional packaging systems such as bottles or blister packs, were insoluble and dispersed completely as fine particles in the mouth within 10 to 15 seconds with a pleasant taste and a good mouth feel.

EXAMPLE 2

| Ingredient | % m/m |
|---|---|
| Microcrystalline cellulose (Avicel PH101) A | 20.00 |
| Levothyroxine sodium B | Therapeutically effective amounts (µg) |
| Maize starch powder | 67.75 |
| Microcrystalline cellulose (Avicel PH101) | 10.00 |
| Citric acid monohydrate powder C | 2.50 |
| Permitted colour powder D | qs |
| Magnesium stearate powder | 0.50 |

The ingredients marked A were triturated. The triturated material was mixed the ingredients marked B. The mixture of A and B was granulated with purified water and dried to form granules, which were (optionally) mixed with the permitted colour (ingredient C). This mixture was finally blended with the magnesium stearate (ingredient D). The final mixture was compressed into tablets each containing 25 µg levothyroxine sodium on an anhydrous basis, each tablet having a hardness in the range from 2 to 6 kp. The resultant tablets were strong enough to survive in conventional packaging systems such as a bottle or blister packs. The tablets were insoluble and dispersed completely as fine particles in the mouth within 10 to 15 seconds with a pleasant taste and mouth feel.

We claim:

1. A solid dispersing dosage form of a pharmaceutical composition for oral administration which disintegrates in the mouth, the dosage form comprising: a therapeutic agent which comprises 0.1 µg to about 10.000 µg of one or more thyroid hormone or hormones; an effective amount of from about 80% to about 99.9% of disintegrating agent by mass; from about 0.01% to about 10% of flavoring agent by mass; and from about 0.1% to about 5% of lubricating agent by mass.

2. A dosage form as claimed in claim 1; in which the thyroid hormone comprises

L-3,5,3',5'-tetraiodothyronine;

L-3,5,3'-triiodothyronine;

L-3,3',5'-triiodothyronine;

L-3,5-diiodothyronine;

pharmaceutically acceptable salts thereof;

or any mixtures thereof.

3. A dosage form as in claim 1, in which the disintegrating agent comprises a blend of at least two components.

4. A dosage form as in claim 3, in which each component independently comprises an ingredient selected from pharmaceutically acceptable starch, modified starch, methyl cellulose, agar, bentonite, cellulose, microcrystalline cellulose, alginic acid, guar gum, carboxymethylcellulose and sodium lauryl sulphate.

5. A dosage form as in claim 1, in which composition comprises an ingredient or ingredients which induces the formation of saliva.

6. A method of treating disorders associated with an impairment of the thyroid hormone function in animals including human beings, which comprises the administration to a patient in need thereof a therapeutically effective amount of a solid oral dosage form which disintegrates in the mouth, said dosage form containing from about 0.1 µg to about 10,000 µg of one or more thyroid hormone or hormones; an effective amount of from about 80% to about 99.9% of disintegrating agent by mass based on the mass of the dose; from about 0.01% to about 10% of flavoring agent by mass based on the mass of the dose; and from about 0.1% to about 5% of lubricating agent by mass based on the mass of the dose.

7. A method for the manufacture of a solid oral dosage form, comprising the steps of:

(a) forming a first mixture by blending in intimate admixture one or more disintegrant or disintegrants with a therapeutic agent comprising one or more thyroid hormone or hormones;

(b) forming a second mixture by blending in intimate admixture one or more disintegrant or disintegrants with a flavouring agent and a lubricating agent;

(c) combining the first and second mixtures to form a pharmaceutical composition; and (d) compressing the composition from step (c) to form a fast dispersing solid oral dosage form.

8. A method of preparing a solid dispersing dosage form of a pharmaceutical composition for oral administration, the method comprising: combining a therapeutic agent which comprises one or more thyroid hormones, and an effective amount of from about 80% to about 99.9% by mass of disintegrating agent based on the mass of the dose; and from about 0.01% to about 10% by mass of flavoring agent based on the mass of the dose; followed by from about 0.1% to about 5% by mass of lubricating agent based on the mass of the dose.

9. A method as in claim 8; in which the thyroid hormone comprises

L-3,5,3',5'-tetraiodothyronine;

L-3,5,3'-triiodothyronine;

L-3,3',5'-triiodothyronine;

L-3,5-diiodothyronine;

pharmaceutically acceptable salts thereof;

or any mixtures thereof.

10. A method as in claim 8, in which the disintegrating agent comprises a blend of at least two components.

11. A method as in claim 10, in which each component independently comprises an ingredient selected from pharmaceutically acceptable starch, modified starch, methyl cellulose, agar, bentonite, cellulose, microcrystalline cellulose, alginic acid, guar gum, carboxymethylcellulose and sodium lauryl sulphate.

12. A method as in claim 8, in which an ingredient or ingredients which induces the formation of saliva is added to the composition.

* * * * *